(12) United States Patent
Binmoeller

(10) Patent No.: US 7,931,693 B2
(45) Date of Patent: Apr. 26, 2011

(54) METHOD AND APPARATUS FOR REDUCING OBESITY

(75) Inventor: Kenneth F. Binmoeller, Rancho Santa Fe, CA (US)

(73) Assignee: Endosphere, Inc., Columbus, OH (US)

( * ) Notice: Subject to any disclaimer, the term of this patent is extended or adjusted under 35 U.S.C. 154(b) by 1251 days.

(21) Appl. No.: 10/999,410

(22) Filed: Nov. 30, 2004

(65) Prior Publication Data

US 2005/0192614 A1  Sep. 1, 2005

Related U.S. Application Data

(60) Provisional application No. 60/547,630, filed on Feb. 26, 2004.

(51) Int. Cl.
*A61F 5/00* (2006.01)

(52) U.S. Cl. ..................... 623/23.64; 606/191

(58) Field of Classification Search .... 623/23.64–23.68, 623/23.7; 600/37; 604/7, 8, 264; 606/191, 606/198, 911
See application file for complete search history.

(56) References Cited

U.S. PATENT DOCUMENTS

| | | |
|---|---|---|
| 2,773,502 A | 12/1956 | Kaslow et al. |
| 4,133,315 A | 1/1979 | Berman et al. |
| 4,134,405 A | 1/1979 | Smit |
| 4,315,509 A | 2/1982 | Smit |
| 4,416,267 A | 11/1983 | Garren et al. |
| 4,485,805 A | 12/1984 | Foster, Jr. |
| 4,501,264 A | 2/1985 | Rockey |
| 4,648,383 A | 3/1987 | Angelchik |
| 4,694,827 A | 9/1987 | Weiner et al. |
| 4,878,905 A * | 11/1989 | Blass .................. 604/891.1 |
| 4,899,747 A | 2/1990 | Garren et al. |
| 5,019,400 A | 5/1991 | Gombotz et al. |
| 5,084,061 A | 1/1992 | Gau et al. |
| 5,234,454 A | 8/1993 | Bangs |
| 5,259,399 A | 11/1993 | Brown |

(Continued)

FOREIGN PATENT DOCUMENTS

DE    4012642 A1    10/1991

(Continued)

OTHER PUBLICATIONS

Binmoeller et al; U.S. Appl. No. 12/174,337 entitled "Conformationally-stabilized intraluminal device for medical applications," filed Jul. 16, 2008.

(Continued)

*Primary Examiner* — Corrine M McDermott
*Assistant Examiner* — Megan Wolf
(74) *Attorney, Agent, or Firm* — Shay Glenn LLP

(57) ABSTRACT

Method and apparatus for treatment of morbid obesity by placement of a series of flow reduction elements in the small intestine to induce satiety are disclosed. The flow reduction elements restrict the movement of partially digested food and reduce the flow rate through the small intestine which causes the emptying of the stomach and the duodenum to occur slower. The flow reduction elements are attached to an elongated tube and are constructed from various shapes and configurations. The flow reduction elements may be inflated with fluid or may be constructed from self-expandable materials. The device is anchored in the antrum of the stomach with an anchoring member. The transoral gastric device can be inserted with a delivery catheter through the working lumen of an endoscope or alongside an endoscope and may be removed with the aid of an endoscope if desired.

58 Claims, 8 Drawing Sheets

U.S. PATENT DOCUMENTS

| | | | |
|---|---|---|---|
| 5,439,476 | A | 8/1995 | Frantzides |
| 5,484,610 | A | 1/1996 | Bae |
| 5,597,797 | A | 1/1997 | Clark |
| 5,820,584 | A | 10/1998 | Crabb |
| 5,868,141 | A * | 2/1999 | Ellias |
| 6,102,922 | A | 8/2000 | Jakobsson et al. |
| 6,160,084 | A | 12/2000 | Langer et al. |
| 6,187,330 | B1 | 2/2001 | Wang et al. |
| 6,264,700 | B1 | 7/2001 | Kilcoyne et al. |
| 6,267,988 | B1 | 7/2001 | Meyer |
| 6,302,917 | B1 | 10/2001 | Dua et al. |
| 6,365,173 | B1 | 4/2002 | Domb et al. |
| 6,388,043 | B1 | 5/2002 | Langer et al. |
| 6,540,789 | B1 * | 4/2003 | Silverman et al. |
| 6,579,301 | B1 | 6/2003 | Bales et al. |
| 6,635,431 | B1 | 10/2003 | Bihain et al. |
| 6,675,809 | B2 | 1/2004 | Stack et al. |
| 6,685,957 | B1 | 2/2004 | Bezemer et al. |
| 6,716,444 | B1 | 4/2004 | Castro et al. |
| 6,720,402 | B2 | 4/2004 | Langer et al. |
| 6,740,121 | B2 | 5/2004 | Geitz |
| 6,746,460 | B2 * | 6/2004 | Gannoe et al. |
| 6,939,557 | B2 | 9/2005 | Rowe et al. |
| 6,946,002 | B2 | 9/2005 | Geitz |
| 6,953,560 | B1 | 10/2005 | Castro et al. |
| 6,981,978 | B2 * | 1/2006 | Gannoe |
| 6,994,095 | B2 | 2/2006 | Burnett et al. |
| 7,025,791 | B2 | 4/2006 | Levine et al. |
| 7,037,344 | B2 | 5/2006 | Kagan et al. |
| 7,111,627 | B2 | 9/2006 | Stack et al. |
| 7,121,283 | B2 | 10/2006 | Stack et al. |
| 7,122,058 | B2 | 10/2006 | Levine et al. |
| 7,175,669 | B2 | 2/2007 | Geitz |
| 7,335,210 | B2 | 2/2008 | Smit |
| 2002/0035347 | A1 | 3/2002 | Bagaoisan et al. |
| 2002/0111648 | A1 | 8/2002 | Kusleika et al. |
| 2003/0040804 | A1 * | 2/2003 | Stack et al. ............ 623/23.7 |
| 2003/0199990 | A1 | 10/2003 | Stack et al. |
| 2004/0015187 | A1 | 1/2004 | Lendlein et al. |
| 2004/0030347 | A1 * | 2/2004 | Gannoe et al. |
| 2004/0044353 | A1 * | 3/2004 | Gannoe |
| 2004/0044354 | A1 | 3/2004 | Gannoe et al. |
| 2004/0088022 | A1 | 5/2004 | Chen |
| 2004/0092892 | A1 * | 5/2004 | Kagan et al. ............ 604/264 |
| 2004/0110285 | A1 | 6/2004 | Lendlein et al. |
| 2004/0122456 | A1 | 6/2004 | Saadat et al. |
| 2004/0153118 | A1 | 8/2004 | Clubb et al. |
| 2004/0219186 | A1 | 11/2004 | Ayres |
| 2004/0267378 | A1 | 12/2004 | Gazi et al. |
| 2005/0004681 | A1 | 1/2005 | Stack et al. |
| 2005/0033331 | A1 * | 2/2005 | Burnett |
| 2005/0033332 | A1 * | 2/2005 | Burnett et al. |
| 2005/0038415 | A1 | 2/2005 | Rohr et al. |
| 2005/0049718 | A1 | 3/2005 | Dann et al. |
| 2005/0055014 | A1 | 3/2005 | Coppeta et al. |
| 2005/0055039 | A1 | 3/2005 | Burnett et al. |
| 2005/0075405 | A1 | 4/2005 | Wilson et al. |
| 2005/0075622 | A1 | 4/2005 | Levine et al. |
| 2005/0080395 | A1 | 4/2005 | Levine et al. |
| 2005/0080431 | A1 | 4/2005 | Levine et al. |
| 2005/0080491 | A1 | 4/2005 | Levine et al. |
| 2005/0090873 | A1 | 4/2005 | Imran |
| 2005/0119674 | A1 | 6/2005 | Gingras |
| 2005/0125020 | A1 | 6/2005 | Meade et al. |
| 2005/0125075 | A1 | 6/2005 | Meade et al. |
| 2005/0183732 | A1 | 8/2005 | Edwards |
| 2005/0238694 | A1 | 10/2005 | Gerhardt et al. |
| 2005/0245719 | A1 | 11/2005 | Mather et al. |
| 2005/0273060 | A1 | 12/2005 | Levy et al. |
| 2005/0277975 | A1 | 12/2005 | Saadat et al. |
| 2006/0020278 | A1 * | 1/2006 | Burnett et al. |
| 2006/0064120 | A1 | 3/2006 | Levine et al. |
| 2006/0079944 | A1 | 4/2006 | Imran |
| 2006/0086362 | A1 | 4/2006 | Solomon |
| 2006/0129237 | A1 | 6/2006 | Imran |
| 2006/0142794 | A1 | 6/2006 | Lendlein et al. |
| 2006/0155311 | A1 | 7/2006 | Hashiba et al. |
| 2006/0161172 | A1 | 7/2006 | Levine et al. |
| 2006/0161265 | A1 | 7/2006 | Levine et al. |
| 2006/0178691 | A1 | 8/2006 | Binmoeller |
| 2006/0259051 | A1 | 11/2006 | Nissl |
| 2006/0265082 | A1 | 11/2006 | Meade et al. |
| 2007/0010864 | A1 | 1/2007 | Dann et al. |
| 2007/0010865 | A1 | 1/2007 | Dann et al. |
| 2007/0027548 | A1 | 2/2007 | Levine et al. |
| 2007/0083271 | A1 | 4/2007 | Levine et al. |
| 2007/0265598 | A1 | 11/2007 | Karasik |
| 2007/0282418 | A1 | 12/2007 | Weitzner |
| 2007/0293885 | A1 | 12/2007 | Binmoeller et al. |
| 2008/0065136 | A1 | 3/2008 | Young |

FOREIGN PATENT DOCUMENTS

| | | |
|---|---|---|
| JP | 01 015063 A2 | 1/1989 |
| WO | WO 89/00407 A1 | 1/1989 |
| WO | WO 03/094785 A1 | 11/2003 |
| WO | WO 2004/041133 A1 | 5/2004 |
| WO | WO2004/093753 A2 | 11/2004 |
| WO | WO 2005/120363 A1 | 12/2005 |
| WO | WO 2006/044640 A1 | 4/2006 |
| WO | WO2008/001381 A2 | 1/2008 |

OTHER PUBLICATIONS

Gao et al., "Sensory and biomechanical responses to ramp-controlled distension of the human duodenum," Am. J. Physiol. Gas., vol. 284, pp. G461-G471 (2003).

French et al., "Is Cholecystokinin a Satiety Hormone? Correlations of Plasma Cholecystokinin with Hunger, Satiety, and Gastric Empyting in Normal Volunteers," Appetite, vol. 16, pp. 95-104 (1993).

Davis et al., "Distension of the small intestine, satiety, and the control of food intake," Am Journal of Clinical Nutrition, vol. 31, pp. S255-S258 (1978).

Read, N.W. "Role of gastrointestinal factors in hunger and satiety in man," Proceedings of the Nutrition Society, vol. 51, pp. 7-11 (1992).

Wilding, J. P. H., "Neuropeptides and appetite control," Diabetes U.K. Diabetic Medicine, vol. 19, pp. 619-627 (2002).

Woods et al., "The Regulation of Food Intake by Peptides," Annals of the New York Academy of Sciences, vol. 575. pp. 236-243 (1989).

Schwartz et al., "Keeping hunger at bay," Nature, vol. 418, pp. 595-597 (2002).

de Castro et al., "A general model of intake regulation," Neuroscience and Biobehavioral Reviews, vol. 26, pp. 581-595 (2002).

Havel, Peter, "Peripheral signals conveying metabolic information to the brain: Short-term and long-term regulation of food intake and energy homeostasis," Society for Experimental Biology and Medicine, vol. 226, pp. 963-977 (2001).

Chapman et al., "Effects of small-intestinal fat and carbohydrate infusions on appetite and food intake in obese and nonobese men," Am J Clin Nutr, vol. 69, pp. 6-12 (1999).

Rayner et al., "Effects of cholecystokinin on appetite and pyloric motility during physiological hyperglycermia," Am J. Physiol. Gastrointest. Liver Physiol. , vol. 278, pp. G98-G104 (2000).

U.S. Appl. No. 60/490,421, filed Feb. 10, 2005, Burnett, Daniel R.*

U.S. Appl. No. 60/525,105, filed Feb. 10, 2005, Burnett, Daniel R.*

Moran et al., "Gastrointestinal satiety signals," Am J Physiol Gastrointest Liver Physiol, vol. 286, pp. G183-G188 (2004).

Read et al., "The Role of the Gut in Regulating Food Intake in Man," Nutrition Reviews, vol. 52, pp. 1-10 (1994).

Rigaud et al., "Gastric distension, hunger, and energy intake after balloon implantation in severe obesity," Int J Obes Relat Metab Disor., Jul; 19(7):489-95 (1995).

Mathus-Vliegen et al., "Intragastric balloon in the treatment of super-morbid obesity. Double-blind, sham-controlled, crossover evaluation of 500-millimeter balloon," Gastroenterology, 99(2): 362-369 (Aug. 1990).

Lindor et al., "Intragastric balloons in comparison with standard therapy for obesity—a randomized, double-blind trial," Mayo Clin Proc 62(11): 992-6 (Nov. 1987).

Standring, Susan (ed). Gray's Anatomy, 39th Ed. 1163-64 (2005).

Kissileff et al., "Cholecystokinin and stomach distension combine to reduce food intake in humans," Am J Physiol Regul Integr Comp Physiol., 285(5):R992-8 (Nov. 2003).

Moran el al, "Neurobiology of cholecystokinin," Crit Rev Neurobiol. 9(1): 1-28 (1994).

Le Quellec et al., "Oxyntomodulin-like immunoreactivity: diurnal profile of a new potential entergastrone," J Clin Endocrinol Metab, 74(6): 1405-9 (Jun. 1992).

Cohen et al., "Oxyntomodulin suppresses appetite and reduces food intake in humans," J Clin Endocrinol Metab., 88(10): 4696-4701 (Oct. 2003).

Schirra et al., Mechanisms of the antidiabetic action of subcutaneous glucagon-like peptide-1(7-36)amide in non-insulin dependent diabetes mellitus, J Endocrinol. 156(1):177-86 (Jan. 1998).

Asakawa et al., "Characterization of the effects of pancreatic polypeptide in the regulation of energy balance," Gastroenterology 124(5):1325-36 (May 2003).

Batterham et al., "Inhibition of food intake in obese subjects by peptide YY3-36," N Engl J Med., 349(10):941-8 (Sep. 4, 2003).

Batterham et al., "Gut hormone PYY(3-36) physiologically inhibits food intake," Nature 418(6898): 650-4 (Aug. 8, 2002).

Caro et al., "Leptin: the tale of an obesity gene," Diabetes 45(11): 1455-62 (Nov. 1996).

Scarpace et al., "Leptin increases uncoupling protein expression and energy expenditure," Am J Physiol., 273 (1 Pt 1): E226-230 (Jul. 1997).

Collins et al., "Role of leptin in fat regulation," Nature, 380 (6576):677 (Apr. 25, 1996).

Schwartz et al., "Model for the regulation of energy balance and adiposity by the central nervous system," Am J Clin Nutr., 69(4): 584-96 (Apr. 1999).

Remington's Pharmaceutical Sciences, 17th Ed., "Freeze-drying," p. 1538-1539.

Batterham et al., "Pancreatic polypeptide reduces appetite and food intake in humans," J Clin Endocrinol Metab. 88(8):3989-92 (Aug. 2003).

D'Alessio et al., "Activation of the parasympathetic nervous system is necessary for normal meal-induced insulin secretion in rhesus macaques," J Clin Endocrinol Metab., 86(3): 1253-9 (Mar. 2001).

Geliebter et al., "Clinical trial of silicone rubber gastric balloon to treat obesity," Int J Obesity, 15(4): 259-266 (1991).

Ghatei et al., "Molecular forms of human enteroglucagon in tissue and plasma: plasma responses to nutrient stimuli in health and in disorders of the upper gastrointestinal tract," J Clin Endocrinol Metab, 57(3):488-95 (Sep. 1983).

Gibbs et al., "Cholecystokinin descreases food intake in rats," J Comp Physiol Psychol. 84(3):488-95 (Sep. 1973).

Havel, PJ, "Role of adipose tissue in body-weight regulation: mechanisms regulating leptin production and energy balance," Proc Nutr Soc. 59(3):359-71 (Aug. 2000).

Haynes et al., "Receptor-mediated regional sympathetic nerve activation by leptin," J Clin Invest. 100(2): 270-278 (Jul. 15, 1997).

Herrmann et al., "Glucagon-like peptide-1 and glucose-dependent insulin-releasing polypeptide plasma levels in response to nutrients," Digestion 56(2):117-26 (1995).

Levin et al., "Decreased food intake does not completely account for adiposity reduction after ob protein infusion," Proc Natl Acad Sci U.S.A., 93(4): 1726-30 (Feb. 20, 1996).

Liddle et al., "Cholecystokinin bioactivity in human plasma. Molecular forms, responses to feeding, and relationship to gallbladder contraction," J Clin Invest. 75(4):1144-52 (Apr. 1985).

Malaisse-Lagae et al., "Pancreatic polypeptide: a possible role in the regulation of food intake in the mouse. (Hypothesis)" Experientia 15; 33(7):915-917 (Jul. 15, 1977).

Näslund et al., "GLP-1 slows solid gastric emptying and inhibits insulin, glucagon, and PYY release in humans," Am J Physiol 277 (3 Pt 2):R910-R916 (Sep. 1999).

Remington: The Science and Practice of Pharmacy, 20th Ed., Chap. 47, Controlled Release Drug Delivery Systems.

Schwartz et al., "Central nervous system control of food intake," Nature, 404(6778): 661-671 (Apr. 6, 2000).

* cited by examiner

METHOD AND APPARATUS FOR REDUCING OBESITY

PRIORITY INFORMATION

This application claims priority to U.S. Provisional Application No. 60/547,630 filed on Feb. 26, 2004, the entire contents of which are hereby expressly incorporated by reference.

BACKGROUND OF THE INVENTION

1. Field of the Invention

The present invention relates to the medical treatment of obesity in humans, and more particularly to apparatus and methods for curbing the appetite of persons being treated for obesity.

2. Description of the Related Art

Extreme obesity is a major health concern in the United States and other countries. Its complications may include hypertension, diabetes, coronary artery disease, stroke, congestive heart failure, venous disease, multiple orthopedic problems and pulmonary insufficiency with markedly decreased life expectancy. Medical management including dietary, psychotherapy, medications and behavioral modification techniques have not yielded exceptional results in multiple trials. Despite the declaration of obesity as a major health problem, the Centers for Disease Control reports that obesity contributes to about 400,000 deaths annually, just behind tobacco (435,000) and ahead of alcohol (85,000), car accidents (43,000) and guns (29,000). Obesity and its complications now account for an estimated 9 percent of U.S. health spending.

Non-surgical approaches for the treatment of obesity include voluntary dieting which is often unsuccessful since most persons do not possess sufficient willpower to limit the intake of food. In addition to behavioral modification, several surgical techniques have been tried which induce malabsorption by reducing the absorptive surface of the small intestine or modify the stomach to reduce a patients desire to eat. Gastric reduction surgeries in which the stomach's volume is reduced had limited early success but often the stomach's size stretches over time so these patients did not exhibit real weight for a sustained period of time. Other surgical approaches combine gastric volume reduction by either partition or bypass with a reduction in the absorptive surface of the small intestine. These procedures may be both hazardous to perform in morbidly obese patients and often create numerous life-threatening postoperative complications. Such procedures typically are invasive, require a long recuperation time and subject the patient to undue pain and discomfort. Also, such operative procedures are often difficult to reverse. These procedures are also expensive and place a large burden on the national health care system.

Other endoscopic approaches include implantation of gastric balloons that prevent overeating by occupying volume within the stomach. This fills a portion of the stomach and provides the patient with a feeling of fullness, thereby reducing food intake. Many problems are associated with the gastric balloon device, including poor patient tolerance and complications due to rupture, migration, and pressure trauma to the gastrointestinal tract. Some sham-controlled studies have failed to show that the gastric balloon was superior to diet alone in achieving weight reduction.

Other devices are designed to attempt to limit the absorption of nutrients in the duodenum by funneling the food through a tube so that the digestive process bypasses portions of the small intestine entirely. By interrupting the intermixing of the digestive fluids and/or limiting the residence period within the stomach, it is believed that the food materials will not fully digest into particles small enough to be absorbed by the body. However these devices have not been evaluated clinically.

Having made the above critical observations, the present invention further recognizes a need for a transoral endoscopic device that mediates physiologic weight loss that is easily inserted into and removed from the gastrointestinal tract, well tolerated by the patient, does not migrate, does not adversely obstruct the lumen, and does not cause tissue injury.

BRIEF SUMMARY OF THE INVENTION

The present invention provides a method and apparatus for treatment of morbid obesity by placement of a series of flow reduction elements in the small intestine to induce satiety. The flow reduction elements are attached along an elongated member which may or may not have a central lumen inside. This elongated member is used to position the flow reduction elements in the small intestine. The length and diameter of the flow reduction section can be selected by the physician to adjust the amount of weight reduction to the patients needs.

The central tube has an anchoring member attached near the proximal end that secures the proximal end in the antrum of the stomach. The anchoring member is sized so that it will not pass through the pyloric valve and so that it secures the central tube and the attached flow reduction elements in proper position in the small intestine. In one embodiment, the anchoring member is constructed of one or more inflatable balloons that when inflated are larger than the pylorus. The anchoring balloons can be deflated for delivery into the stomach and removed through the working lumen or alongside an endoscope. In another embodiment the anchoring member is an expandable umbrella-like skeleton frame that is attached to the flexible tube. The large end of the umbrella faces the pylorus and the frame can be collapsed for delivery and recovery.

The flow reduction elements can have various shapes and may be attached at various points along the central tube. The flow reduction elements may be inflated with fluid through a fluid connection with the central tube or may be constructed from self-expandable material such as a foam or spring structure. The space occupying flow reduction elements may also be filled or impregnated with pharmacologics, biochemicals, alimentary lipids, alimentary peptides or metabolic substances that release into the small intestine to further provide feelings of satiety.

The transoral gastric device can be inserted with a delivery catheter through the working lumen of an endoscope or alongside an endoscope and may be removed with the aid of an endoscope if desired.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1:
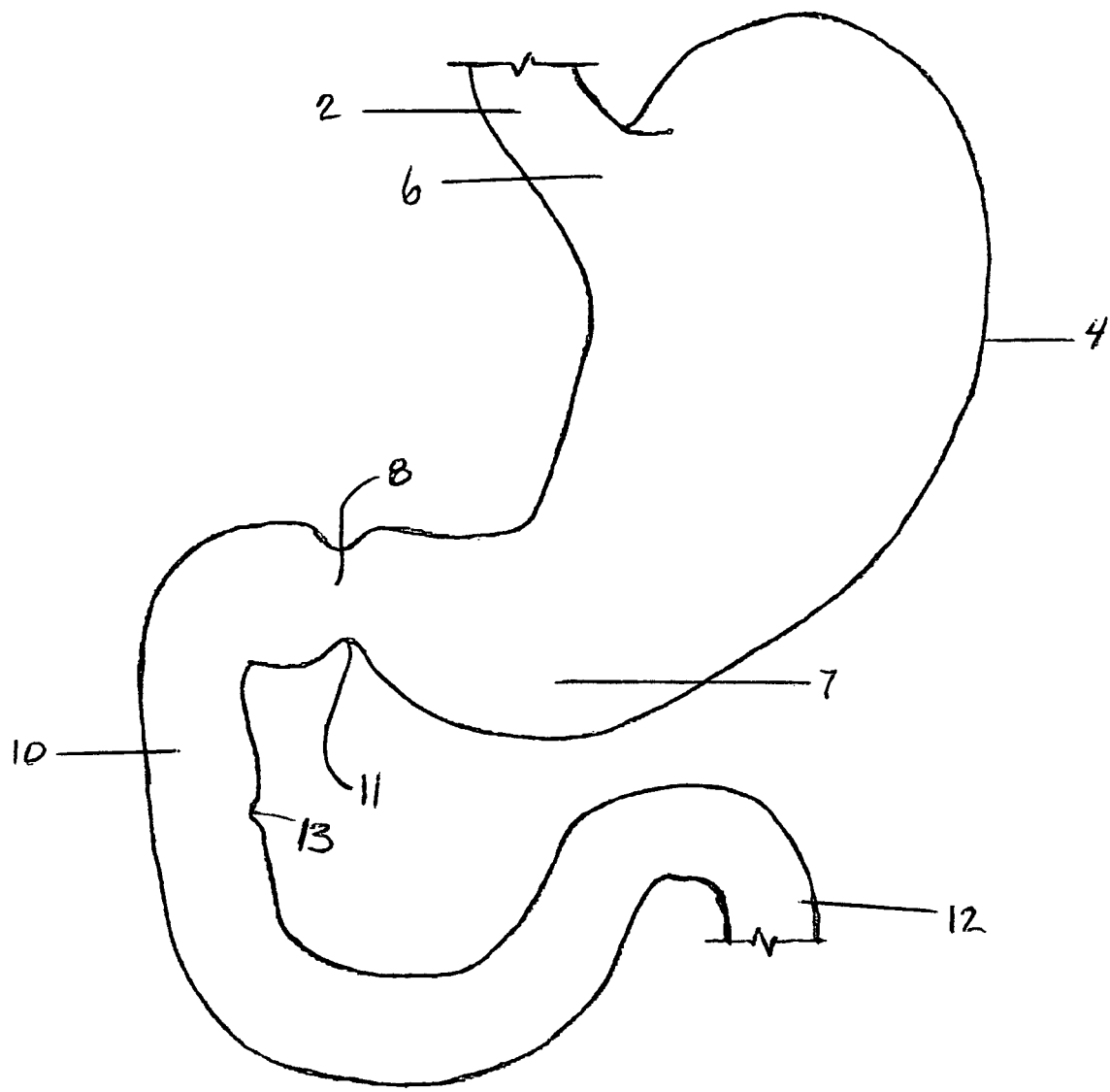
FIG. 1 is a general drawing of the stomach and adjacent parts of the alimentary canal.

FIG. 1 shows the human stomach and small intestine. Important features are the esophagus 2, stomach 4, antrum 7, pylorus 8, pyloric valve 11, duodenum 10, jejunum 12 and ampulla of Vater 13. The esophagus 2 terminates at the nose or mouth at its superior end and at the stomach 4 at its inferior end. The stomach 4 encloses a chamber which is characterized, in part, by the esophageal-gastric juncture 6, which is an opening from the esophagus 2 at one end, and the antrum-pyloric juncture 5 which is a passageway between the antrum 7 through the pylorus 8 to the duodenum 10 at the other end. Specifically, the pylorus 8 controls discharge from the stomach 4 by a sphincter muscle, the pyloric valve 11, which enables the pylorus 8 to open wide enough to pass an object which is approximately one cubic centimeter or less. Gastric contents, after passing into the duodenum 10, continue on into the jejunum 12 and on into the ileum (not shown). The duodenum 10, jejunum 12 and ileum make up what is known as the small intestine. However these individual portions of the alimentary canal are sometimes individually referred to as the small intestine. In the context of this invention the small intestine refers to all or part of the duodenum, jejunum and ileum. The ampulla of Vater 13 is shown as a small protrusion on the medial wall. Bile and pancreatic fluids enter the duodenum 10 at this point to further aid digestion.

The duodenum 10 comprises the first nine to ten inches of the small intestine and is the only portion of the small intestine which is attached to the back wall of the abdominal cavity (retroperitoneum). The remainder of the small intestine is not attached to the body, but merely folds freely in a sack called the mesentery, which is contained within the peritoneum. The digestive process starts when food materials are mixed with saliva and enzymes in the mouth. The digestive process continues in the stomach 4, where the food is combined with acids and additional enzymes to liquefy the food. This food resides in the stomach 4, for a short time and then it passes into the duodenum 10 to be intermixed with bile and pancreatic juice, which make the nutrients contained therein available for absorption by the villi and microvilli of the small intestine or by other absorptive organs of the body.

The present invention understands that if the passage of partially digested food as described is partially blocked and the flow rate through the small intestine is reduced, then the emptying of the stomach and the duodenum will occur slower. This in turn will create a feeling of satiety and will decrease the consumption of food by an obese patient.

Additionally, because a large amount of the nutritional absorption occurs in the small intestine, if the amount of absorptive surface area of the walls of the small intestine is restricted or blocked, thus interrupting or reducing the intermixing of the digestive fluids, the partially digested food materials are not readily absorbed by the small intestine or other absorptive organs of the body. The partially digested food materials are then passed to the large intestine for elimination from the body with limited caloric absorption by the body.

Furthermore, the present invention understands that if the physical characteristics of the device and/or a reduction of flow rate of food breakdown products through the small intestine results in distension of the small intestine, or increases the contact time between the small intestine and the partially digested food then this distension or increased contact time may activate osmoreceptors that may release hormones and neurotransmitters such as cholecystokinins (CCK) and neural signals that may induce satiety.

Figure 2:
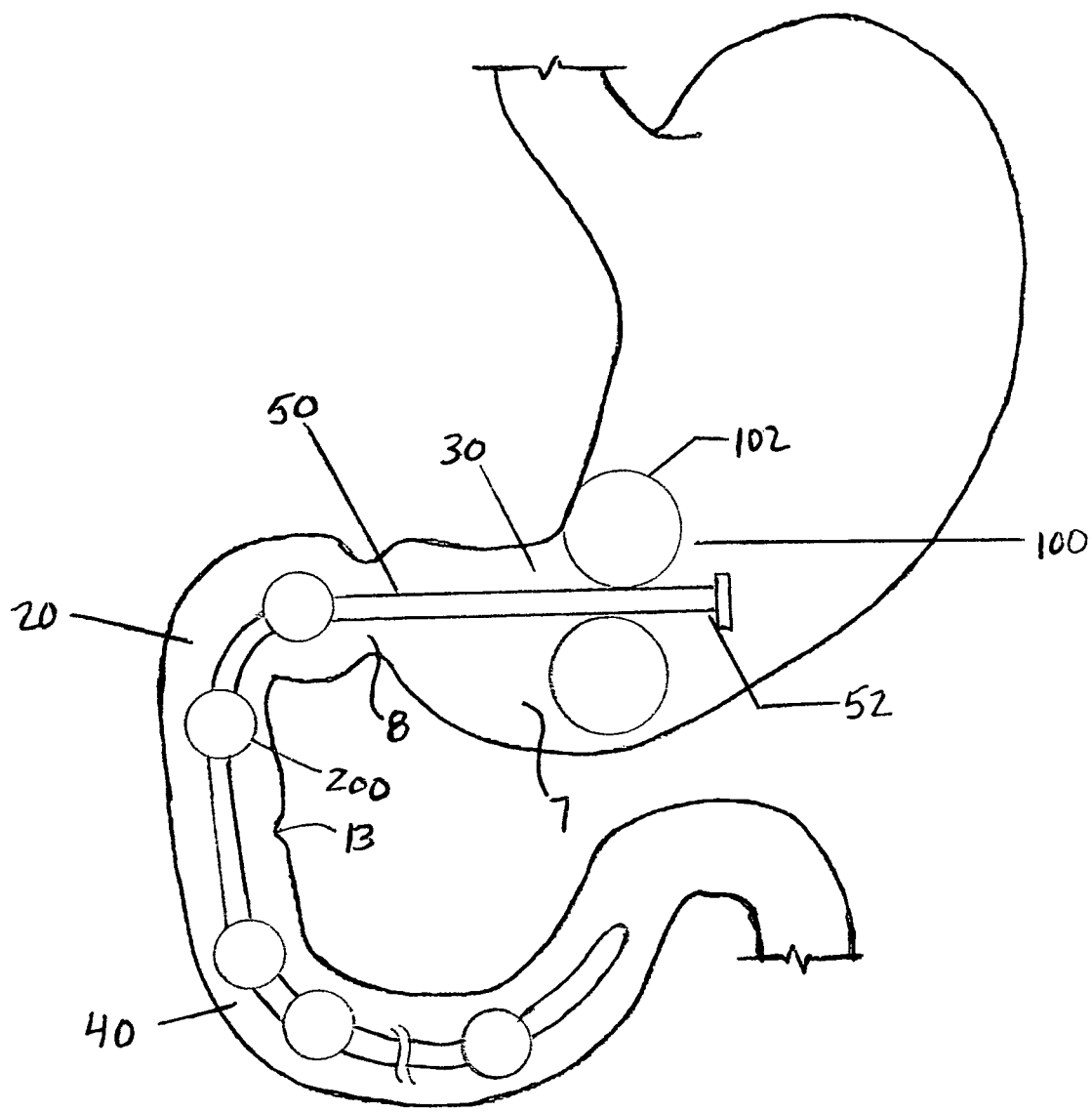
FIG. 2 is a perspective view of a duodenal/small intestinal insert in accordance with the present invention positioned inside the stomach and small intestine.

FIG. 2 shows an exemplary non-limiting small intestinal insert 20 made in accordance with the present invention in position in the stomach and small intestine. The insert has a proximal portion 30 and a distal portion 40. The insert has a central tube 50 that extends between the proximal portion 30 and the distal portion 40. A series of flow reduction elements 200 can be attached to the distal portion of the central tube and may be sized to fit inside the small intestine. However the area of the central tube 50 near the ampulla of Vater 13 has no flow reduction elements 200 to prevent blockage of the ampulla of Vater. The central tube preferably has an anchoring member 100 attached near a proximal end 52 of the central tube 50, with the anchoring member 100 securing the proximal end 52 of the central tube 50 in the antrum 7 of the stomach. The anchoring member 100 is sized so that it will not pass through the pylorus 8, so that it can maintain the flow reduction elements 200 in proper position in the small intestine. In one embodiment, the anchoring member can be established by one or more inflatable balloons 102 that when inflated are larger than the pylorus 8. The inflatable balloons 102 can be deflated for delivery into the stomach and then inflated inside the stomach. The inflatable balloons 102 can also be later deflated for removal using endoscopic techniques.

Figure 3:
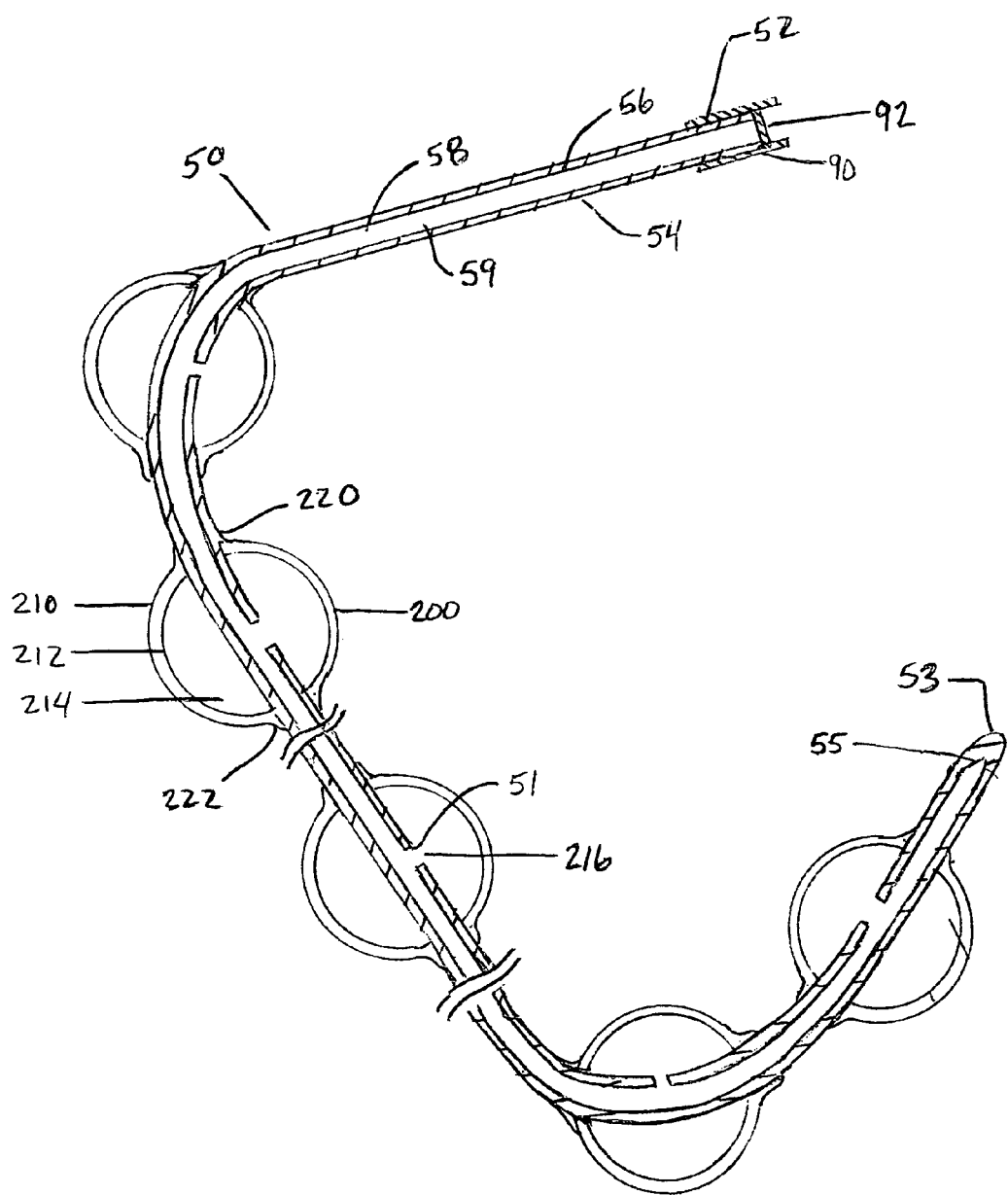
FIG. 3 is a partial section view of a central tube illustrating attached flow reduction elements and central lumen.

FIG. 3 shows the central tube 50 with the flow reduction elements 200 attached. The central tube 50 can be flexible and constructed of polymeric material that can be easily formed or extruded and delivered with the aid of an endoscope by known techniques. A central tube 50 that is soft and flexible will contour to the anatomy of the gastrointestinal tract and provide less irritation of the stomach lining. The central tube 50 can be made from polymers such as nylon, polyolefins, polyurethane, silicone or polyvinyl chloride (PVC). The central tube polymer needs to be compatible with the chemical environment of the gastrointestinal tract and should provide enough structural integrity to prevent migration of the flow reduction elements in response to peristaltic action in the bowel. If desired, however, the central tube 50 can deploy to a fixed configuration so that once properly positioned it will maintain a steady position despite peristaltic movement of the stomach and small intestine. For example, the fixed configuration could be the shape that the duodenum 10 and jejunum 12 naturally assume in the abdomen.

The length of the central tube 50 can be established depending on the therapeutic result desired and the patient's anatomy. For example, the central tube 50 and the attached flow reduction elements 200 may extend into a portion of or through the entire duodenum 10. On some patients the central tube 50 and the attached flow reduction elements 200 may extend past the duodenum 10 and into the jejunum 12. It is anticipated that several lengths might be used by a physician to treat the various body types and metabolic demands. For example, if a patient is 20% overweight, the physician might select a length of central tube 50 with its attached flow reduction elements 200 that permits absorption of only 80% of the nutritional potential of a typical daily intake of calories. The reduction of caloric intake over time will lead to weight loss.

FIG. 3 shows a central tube 50 with an outer wall 54 and an inner wall 56 that define an interior space 58. The interior space 58 forms an inner lumen 59 that may be continuous from the proximal end 52 to just short of the distal end 53 of the central tube 50. The distal end 53 of the central tube 50 is sealed at a point 55 so that fluid introduced into the central tube 50 does not leak out distally into the small intestine. In some embodiments a valve 90 can be located substantially at the proximal end of the inner lumen 59. The valve 90 may be a self sealing valve that has a septum 92 that can be accessed by a needle or blunt tip tube for introduction of fluid into the inner lumen 59. The valve 90 also can be accessed so that the fluid inside the inner lumen 59 of the central tube 50 can be aspirated for removal. It is to be understood that the valve type is not limited to a septum type valve only, and that other types of mechanical valves may also be used in place of the septum valve described.

As shown in FIG. 3 and as mentioned above, one or more flow reduction elements 200 can be attached to the central tube 50. In some embodiments the diameter of each flow reduction element 200 can be concentric with the axis of the central tube 50. Each flow reduction element 200 has an outer wall 210, an inner wall 212, and an inner space 214 is established inside the inner wall 212. At or near its proximally-oriented surface 220 and also at or near its distally-oriented surface 222, each flow reduction element 200 can be attached to the central tube 50 with the inner space 214 of the flow reduction element 200 in fluid communication with the lumen 59 of the central tube 50, such that the inner space 214 surrounds the outer wall 54 of the central tube 50. Each flow reduction element 200 may be attached to the central tube 50 by adhesives, heat bonding, mechanical restraint or other suitable methods.

As shown in FIG. 3, the central tube 50 can be formed with plural inlet/exit ports 216 that are located inside respective flow reduction elements 200. More specifically, each port 216 is formed completely through the central tube wall 51 to establish a pathway for fluid communication between the inner lumen 59 of the central tube 50 and the inner space 214 of the respective flow reduction element 200. Consequently, the inner lumen 59 of the central tube 50 may be used to introduce fluid into the inner spaces 214 of the flow reduction elements 200 and to inflate the flow reduction elements 200 from a collapsed configuration, in which insertion and removal of the flow reduction elements 200 is facilitated, to an inflated configuration shown in FIG. 3, in which resistance to food passage is increased to induce satiety. Thus, the flow reduction element or elements 200 in this embodiment act as balloons that can be deflated and collapsed around the central tube 50 for introduction into the small intestine and then inflated to the desired diameter once in position.

Each flow reduction element or elements 200 can either be elastic balloons or inelastic balloons. When an elastic balloon material is used to establish a flow reduction element 200, the flow reduction element 200 inflates to a diameter that is dependent on the volume of fluid introduced into the inner space of the flow reduction element. This embodiment permits adjustment of the balloon size as determined by the physician. If the balloon is too small, for instance, additional fluid could be introduced to enlarge the balloon diameter. Alternatively, if the balloon is too large, additional fluid could be removed to shrink the balloon diameter. It is understood that an alternate embodiment consisting of an inelastic balloon inflates to a diameter that is independent of the volume of fluid introduced into the inner space of the sphere. The diameter of this type of balloon is fixed when manufactured and does not permit in situ adjustment of the balloon size. However, this type of balloon prevents possible over inflation and rupture if too much fluid is introduced into the balloon.

The flow reduction elements 200 shown in FIG. 3 have the shape of a round sphere. However, other shapes are contemplated and any shape that effectively functions to inhibit the passage of partially digested food into the small intestine is acceptable. It is understood that the ability of the small intestinal insert 20 to remain within the small intestine can be affected by the shape, orientation and tautness of the flow reduction elements 200. For example alternate shapes such as ovoid, elliptical, elongated ellipse and even irregular non-geometrical shapes are potentially feasible.

Figure 4:
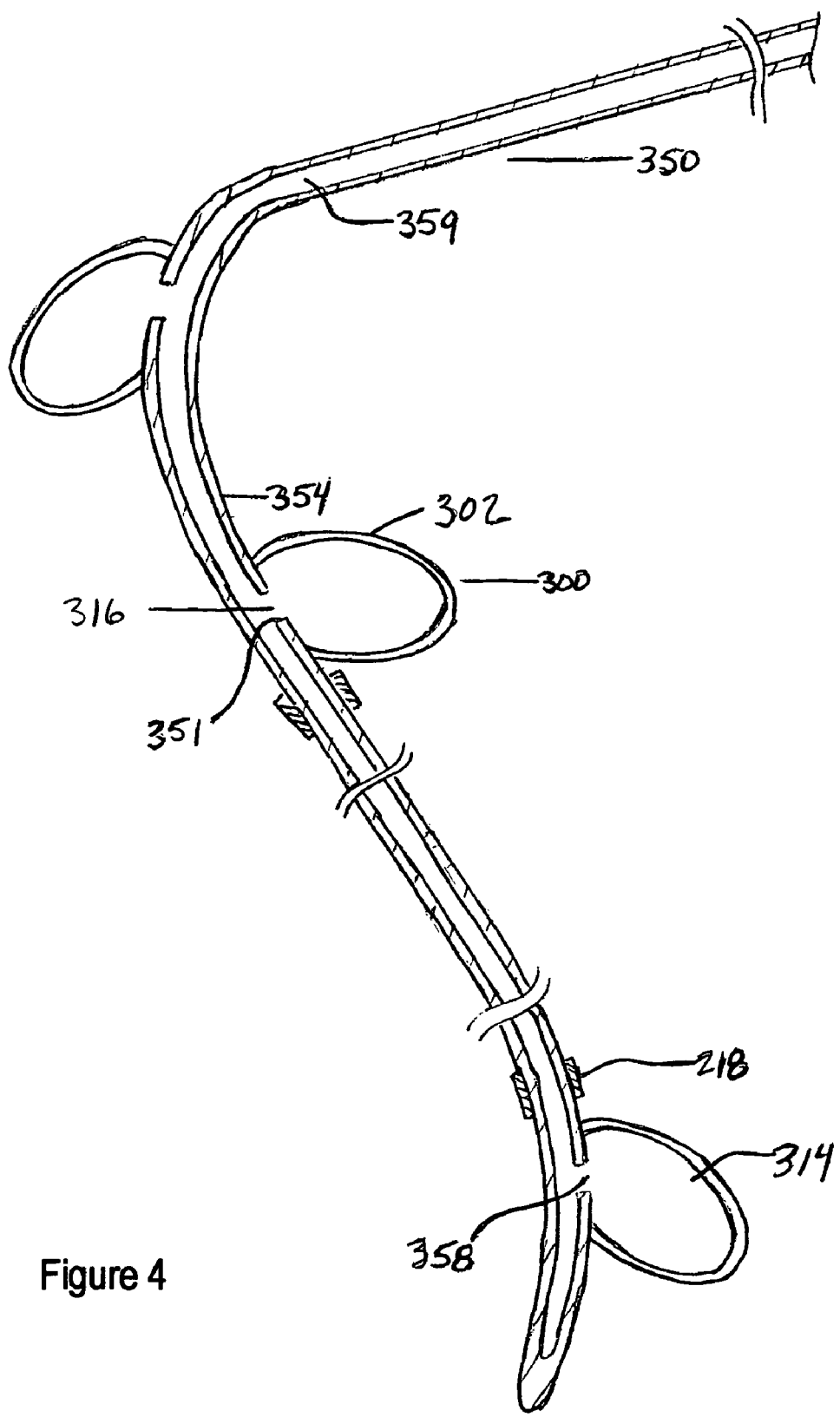
FIG. 4 is a partial section view of a central tube illustrating eccentrically attached flow reduction elements and central lumen.

FIG. 4 illustrates an alternative embodiment of the present invention in which one or more flow reduction elements 300 are eccentrically attached to a central tube 350. In this embodiment the axis or diameter of the flow reduction element or elements 300 is not concentric with the axis of the central tube. The outer wall 302 of the flow reduction element is attached to the side of an outer wall 354 of the central tube 350. An inner space 314 of each flow reduction element 300 is eccentric relative to the axis of the central tube 350 and is in fluid communication with an inner lumen 359 of the central tube 350 through a respective opening 316. As was the case with the embodiment shown in FIG. 3, in the embodiment shown in FIG. 4 the inner lumen 359 can be used to introduce and remove fluid into the inner space 314 of the flow reduction element 300 to move the flow reduction element 300 between inflated and collapsed configurations.

In this context the flow reduction elements 300 can be inflated with a fluid, either liquid or gas. Preferably the gas is air, nitrogen or carbon dioxide and the liquid is preferably water or water mixed with other solutions. It is important for the physician to monitor the flow reduction element 300 location in the small intestine and the diameter of the flow reduction element relative to the diameter of the small intestine. The flow reduction element can be inflated with a radiopaque fluid that is visible on X-ray. If the flow reduction element containing the radiopaque fluid is visible on x-ray, the physician can non-invasively visualize the flow reduction element size from outside the patient's body. This knowledge enables the physician to adjust the size of the flow reduction element by injecting additional fluid into the flow reduction element through the inner lumen 59 as required. Likewise radiopaque marker bands 218 as shown in FIGS. 3 and 4 can be placed around the central tubes 50 and 350 respectfully to facilitate visualization of the central tube's location in the small intestine. The radiopaque marker bands 218 can be placed at predetermined intervals so that the distance inside the small intestine can be used as depth markers and can be measured from outside the body.

Figure 5:
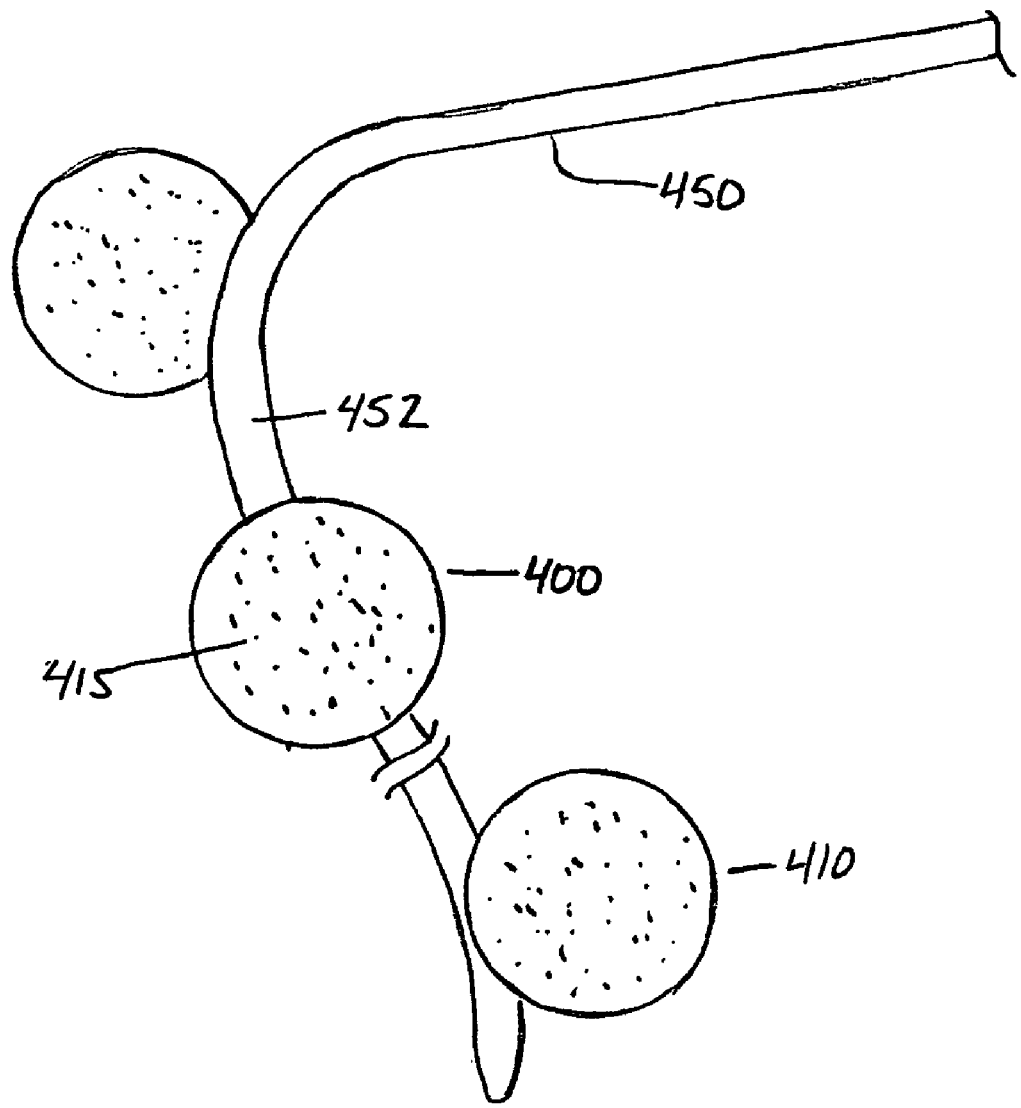
FIG. 5 is a perspective view of an alternative embodiment showing an elongated member and illustrating attached flow reduction elements.

FIG. 5 shows an alternative embodiment with a central shaft 450 around which first flow reduction elements 400 are concentrically attached and second flow reduction elements 410 are eccentrically attached. The element 400 can be attached to the central shaft 450 in any manner as described previously. The flow reduction elements 400 are made from material that can be folded or collapsed to a first volume suitable for insertion with the aid of an endoscope and then self expand to a second volume suitable for restricting the flow of partially digested food according to the present invention. The flow reduction elements can be made from materials such as sponge, foam, hydrogels or springs. These materials can be compacted into a small volume and then self expand to a pre-determined shape and volume when unrestricted. The central shaft 450 can be solid and without an inner lumen or inner space. Because the flow reduction elements self expand, the need for an inflation system is eliminated and this embodiment represents a simple mechanical design. The flow reduction elements are attached mechanically, by heat fusing, adhesives or other suitable methods as known in the art.

The surface of the flow reduction element 415 and outside walls of the central tube 452 may be filled or coated with slow release medicaments, enzymes, cofactors, pharmacologics, biochemicals, alimentary lipids, alimentary peptides or metabolic substances. These substances are designed to release over time into the intestine to modify the biochemical processes or trigger alternative receptor sites that in turn will alter the digestive process.

Figure 6:
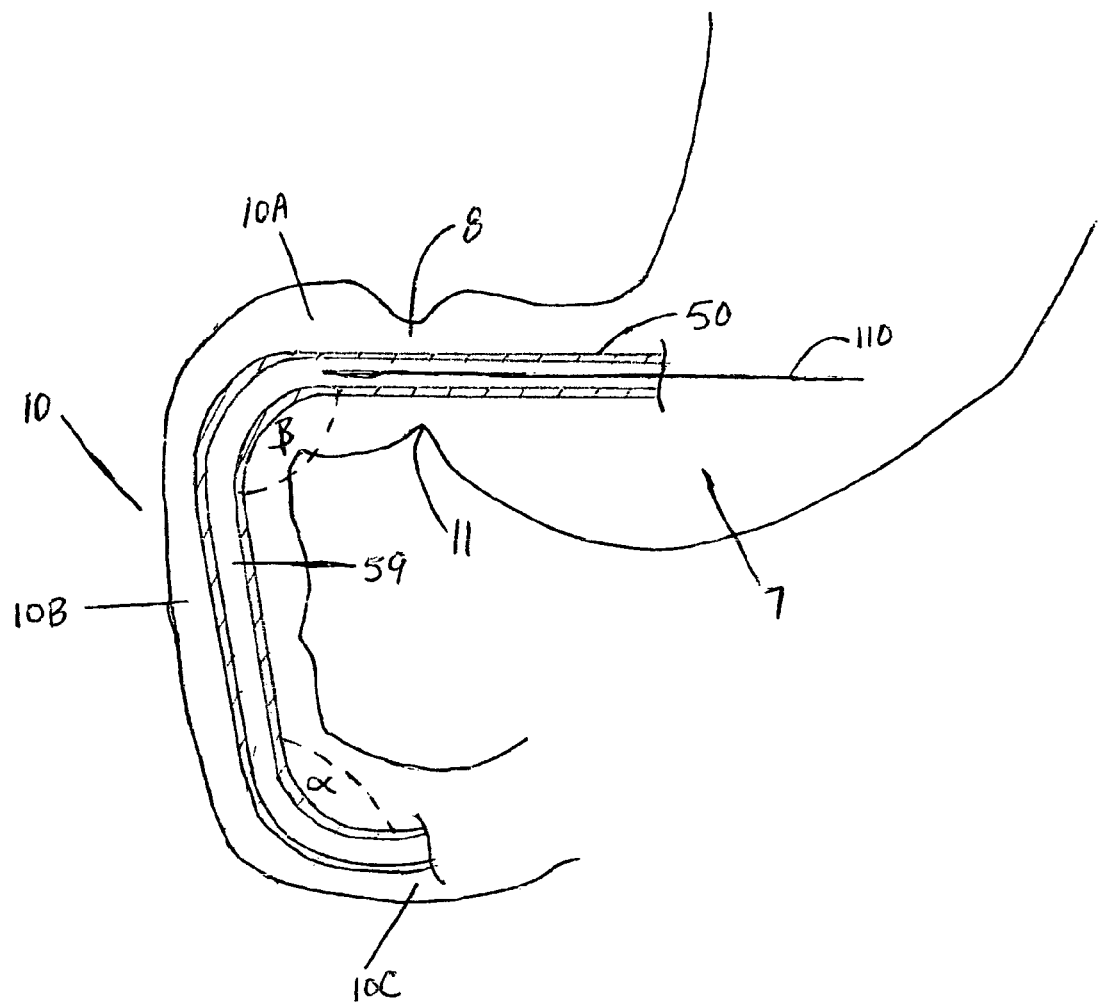
FIG. 6 is a section view of the central tube inside of the pylorus and small intestine.

FIG. 6 shows the central tube 50 in the antrum 7, pylorus 8 and the duodenum 10; consisting of three parts, the duodenal bulb 10A, the vertical duodenum 10B, and the horizontal duodenum 10C. The flow reduction elements have been removed from FIG. 6 for clarity. The central tube 50 is shown traversing the pyloric valve 11. It is important that the diameter of the central tube not obstruct the pyloric valve opening so that the valve can still function normally. The central tube diameter should be in the range of 5 to 7 French. Distal to the pylorus 8 and immediately after entering the duodenum 10 the central tube 50 can assume a sharp bend of radius β between the duodenal bulb 10A and the vertical duodenum 10B, and a sharp bend of radius α between the vertical duodenum 10B and horizontal duodenum 10C. Preferably the radius β and the radius α may be between 45° and 110°. More preferably, the radius β and the radius α may be between 60° and 100° such that the central tube 50 bends to follow the inner lumen of the duodenum 10 at this these locations. It is advantageous that the central tube 50 be flexible enough to conform to this sharp angulation to avoid kinking. In another embodiment the central tube 50 can be pre-formed with a configuration that conforms to the duodenal angulations prior to insertion in the body and is constrained in a straight configuration by a stiffening rod 110 placed down the inner lumen 59 of the central tube 50 as shown. This stiffening rod 110 is placed into a separate lumen designed to house this stiffening rod or imbedded in the wall of the central tube 50. Upon insertion into the patient with the aid of an endoscope, when the central tube 50 reaches the location of the sharp bends in the duodenum 10, the stiffening rod 110 is withdrawn, thereby allowing the central tube 50 to assume the pre-formed shape. In another embodiment, the central tube 50 may have a shape memory alloy wire imbedded inside the central tube wall 51 or residing in the inner lumen 59. This shape memory alloy wire has a pre-set bend configuration with a radius β and a radius α that matches the bend configuration of the duodenum and is positioned in the central tube 50 at the corresponding location. Upon insertion into the patient with the aid of an endoscope, when the central tube 50 reaches the location of the sharp bend in the duodenum 10 and the shape memory alloy wire reaches a pre-set transition temperature equal to the temperature of the small intestine or 37° Fahrenheit, the wire assumes the programmed shape and forces the central tube 50 and the central tube wall 51 to assume the same shape. In another embodiment, the central tube 50 may have a spring embedded inside the central tube wall 51 or inner lumen 59. This spring could be pre-shaped to the anatomy of the wall of the small intestine. The spring is held straight during delivery and conforms to the small intestine anatomy after release. The shape enables the device to remain in place.

Figure 7:
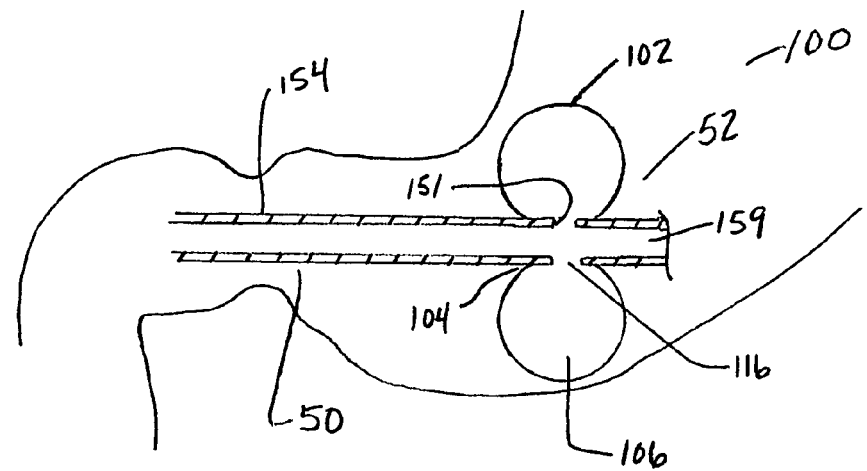
FIG. 7 is a perspective section view of a central tube and an anchoring member.

Turning to various anchoring members 100 that can be used, as shown in FIG. 7, the central tube 50 has an anchoring member 100 attached near the proximal end 52. The anchoring member 100 can be established by one or more inflatable balloons 102. These balloons 102 can be eccentrically attached to the central tube at point 104 near the proximal end 52 of the central tube 50. These balloons can be formed in many shapes and are not limited to the spherical shape shown. The central tube can be formed with an opening 116 for each respective balloon 102 so that a pathway for fluid communication is established between the inner lumen 59 of the central tube 50 and the inner space of each balloon 106. The inner lumen 59 is used to introduce fluid into the inner space of the balloon 106 and inflate the balloon 102 from a first volume in a collapsed state to a second volume or inflated state.

When the anchoring member 100 is fully inflated, it secures the proximal end of the central tube 52 in the antrum of the stomach. The inflatable balloons 102 have a combined cross sectional diameter greater than the diameter of the pyloric valve 11 to prevent migration across the pylorus. The inflatable balloons 102 can be inflated and deflated by adding or removing fluid from the central tube inner lumen 59. The inflatable balloons 102 may be connected to the same central tube inner lumen 59 as flow reduction elements 200 and 300 as shown in FIGS. 3 and 4, and can be inflated simultaneously and deflated simultaneously. However, the central tube 50 may have more than one inner lumen so that the inflatable balloons 102 and individual flow reduction elements 200 and 300 may be inflated and deflated independently from each other.

Figure 8:
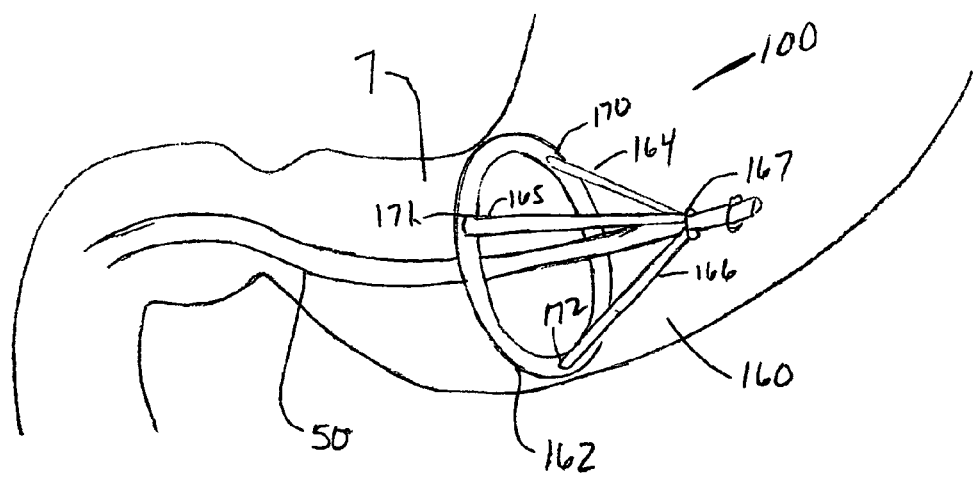
FIG. 8 is a perspective view of an alternative embodiment of a central tube and an anchoring member.

FIG. 8 illustrates another embodiment of the anchoring member 100 deployed in the antrum 7. A central tube 50 is attached to an inverted umbrella skeleton 160. This skeleton 160 has a ring 162 that surrounds the central tube 150 and is supported by three struts 164, 165 and 166. These struts are joined together at the central tube 50 at point 167 and attached to the ring 162 at points 170, 171 and 172. Although three struts are illustrated in FIG. 8, it is possible to construct the anchoring member 100 with one or more struts. The ring 162 is made from flexible plastic material or flexible wire and has a diameter significantly larger than the diameter of the pyloric valve 11. The umbrella skeleton 160 is collapsed around the central tube 50 for insertion into the stomach with the aid of an endoscope. As the device is released from the endoscope, the umbrella skeleton 160 springs out and assumes a configuration shown in FIG. 8. The struts 164, 165 and 166 may be made from plastic, metal or from plastic covered metal. The edge of the ring which is in contact with the antrum walls 163, may be constructed to assist in securing the umbrella ring 162 to the walls of the antrum. The surface may be roughened to increase surface friction or the wall may have protrusions or barbs that physically attach to the stomach lining.

Figure 9B:
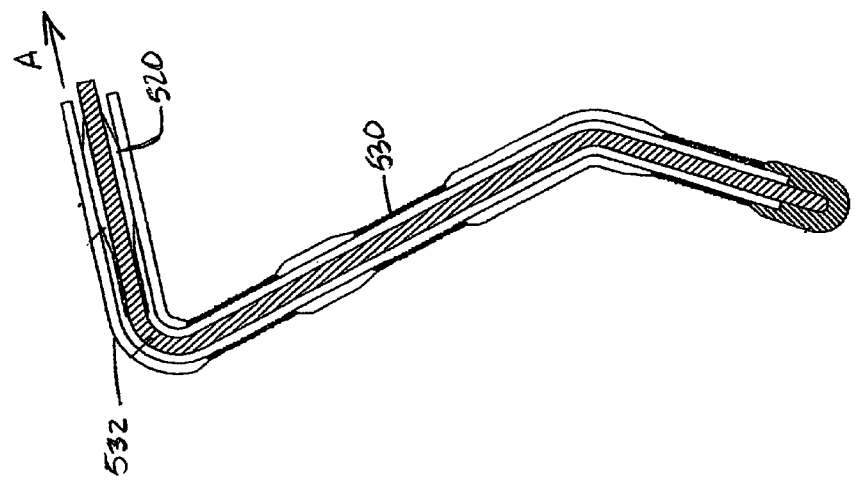
FIG. 9b is a section view of alternative embodiment of the current invention shown in a collapsed configuration.
Figure 9A:
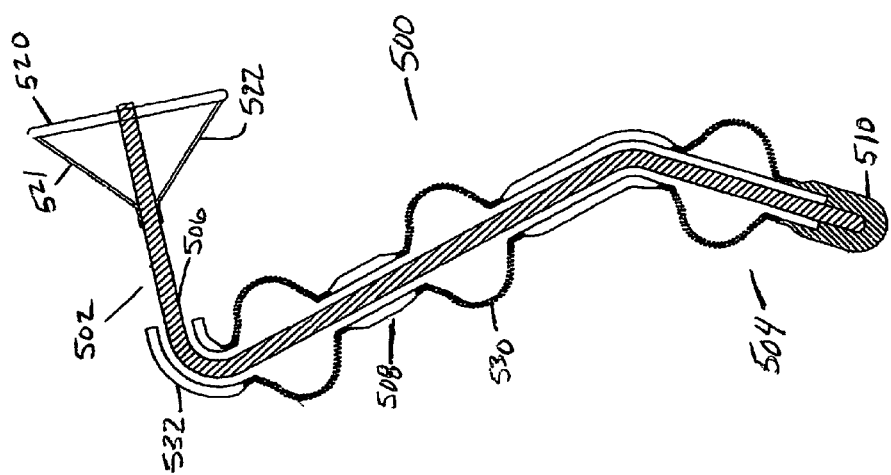
FIG. 9a is a section view of alternative embodiment of the current invention.

FIG. 9 illustrates another embodiment of the current invention. FIG. 9a depicts a duodenal/small intestinal insert 500 with a proximal portion 502 and a distal portion 504 shown in an expanded state. In this embodiment, a central shaft 506 is attached to an expandable sleeve 508 at the sleeve distal end 510 near the distal portion 504 of the duodenal/small intestinal insert. The opposite end of the central shaft 506 is attached to a toroid anchoring member 520. The anchoring member 520 is attached at the central shaft 506 with two connecting struts 521 and 522. More than two connecting struts may be employed to securely attach the toroid anchoring member 520 to the central shaft 506. The anchoring member 520 is shaped like a funnel that is designed to seat in the Pylorus without obstructing its function. The central shaft 506 may be pre-formed to have a configuration that conforms to the anatomy of the duodenum 10 shown in FIG. 6. A central shaft 506 so described would also force the expandable sleeve 508 to assume the configuration of the shaft 506. The central shaft 506 may be constructed out of wire, spring, shape memory alloys, hollow steel tubing or plastic polymers. The expandable sleeve is comprised of at least one flow reduction element 530 and a connecting tube 532. The flow reduction element 530 can be formed using springs or polymer materials. The flow reduction element 530 maybe formed from a spring and then covered with a flexible polymer to prevent partially digested food from entering the flow reduction element 530. The flow reduction element 530 can be formed with a preset curved shape which can be straightened out for insertion with the aid of an endoscope. The flow reduction element 530 diameter is sized to the small intestine diameter. FIG. 9b illustrates the connecting tube 532, anchoring member 520 and the flow reduction element 530 in a collapsed configuration for insertion into the small intestine. In this configuration the connecting tube 532 and the expandable sleeve 508 have been drawn toward the proximal end of the central shaft 506. The connecting tube 532 also covers the collapsed anchoring member 520. This movement of the connecting tube 532 relative to the central shaft 506 occurs because the flow reduction element 530 is collapsed in response to a force A applied to the connecting tube 532. It is anticipated that the connecting tube 532 can be pulled toward the proximal portion 502 of the central shaft to collapse the insert for insertion into the small intestine with the aid of an endoscope. Once in position, the force A is removed, the connecting tube 532 returns toward the distal portion 504 of the insert which releases the anchoring member 520 from its constraint and allows the expandable sleeve 508 to expand to its original diameter.

This invention has been described and specific examples of the invention have been portrayed. The use of those specifics is not intended to limit the invention in anyway. Additionally, to the extent that there are variations of the invention, which are within the spirit of the disclosure or equivalent to the inventions found in the claims, it is my intent that this patent will cover those variations as well.

I claim the following:

1. A duodenal/small intestinal insert for treating obesity in humans by reducing the desire for eating, comprising:
    an elongated solid central shaft member, said elongated solid central shaft member having a proximal end and a distal end and a curved longitudinal axis extending from the proximal end to the distal end, wherein the elongated solid central shaft member has a pre-set shape prior to insertion in the gastrointestinal tract such that a portion of the curved longitudinal axis mimics an angulation of the duodenum and returns to the pre-set shape after insertion into the gastrointestinal tract
    an anchoring member engaged with the proximal end of said elongated solid central shaft member; and
    at least one flow reduction element coupled to the elongated solid central shaft member at a distance from the anchoring member such that when the anchoring member is in an antrum of the stomach the at least one flow reduction element is positioned within a small intestine.
2. A duodenal/small intestinal insert of claim 1, wherein a portion of the elongated solid central shaft member between the anchoring member and the flow reduction element is rigid.
3. A duodenal/small intestinal insert of claim 1, wherein a portion of the elongated solid central shaft member between the anchoring member and the flow reduction element is flexible.
4. A duodenal/small intestinal insert of claim 1, wherein the elongated solid central shaft member is formed from a shape memory material.
5. A duodenal/small intestinal insert of claim 1, wherein the elongated solid central shaft member contains a shape memory material.
6. A duodenal/small intestinal insert of claim 1, wherein the flow reduction element is concentric with the elongated solid central shaft member.
7. A duodenal/small intestinal insert of claim 1, wherein the flow reduction element is eccentric to the elongated solid central shaft member.
8. A duodenal/small intestinal insert of claim 1, wherein the flow reduction element can be inflated from a first volume to a second volume with a fluid.
9. A duodenal/small intestinal insert of claim 8, wherein the fluid is a gas.
10. A duodenal/small intestinal insert of claim 1, wherein the flow reduction element occupies about 30-80% of the small intestine diameter.
11. A duodenal/small intestinal insert of claim 1, wherein the flow reduction element occupies about 40-60% of the small intestine diameter.
12. A duodenal/small intestinal insert of claim 1, wherein the flow reduction element is sized to restrict but not occlude the movement of digested food through the small intestine.
13. A duodenal/small intestinal insert of claim 1, wherein the flow reduction element self expands from a first volume to a second volume when unrestrained.
14. A duodenal/small intestinal insert of claim 13, wherein the flow reduction element is formed from open or closed cell foam.
15. A duodenal/small intestinal insert of claim 1, wherein the flow reduction element is impregnated with pharmacologics, biochemicals, alimentary lipids, alimentary peptides or metabolic substances.
16. A duodenal/small intestinal insert of claim 15, wherein the pharmacologics, biochemicals, alimentary lipids, alimentary peptides or metabolic substances are released into the small intestine over time.
17. A duodenal/small intestinal insert of claim 1, wherein the anchoring member is a toroid shaped anchoring member configured to reside in the antrum of the stomach and when fully deployed restricts distal migration of the elongated member.
18. A duodenal/small intestinal insert of claim 1 wherein the anchoring member comprises two or more balloons eccentrically arranged on the proximal end of the elongated solid central shaft member.
19. A duodenal/small intestinal insert of claim 18, wherein the balloons are inflatable and their combined diameter is larger than the opening of the pylorus.
20. A duodenal/small intestinal insert of claim 1, wherein the anchoring member comprises two or more volume occupying members that self expand from a first volume to a second volume when unrestrained and their combined diameter is larger than the opening to into the pylorus.
21. A duodenal/small intestinal insert of claim 1, wherein the anchoring member comprises:
    a collapsible, umbrella cage with a closed end and an open end, said closed end connected to the proximal end of the elongated solid central shaft member.

22. The duodenal/small intestinal insert of claim 21, wherein the umbrella cage is constructed from a shape memory material.

23. The duodenal/small intestinal insert of claim 21, wherein the umbrella cage is constructed from a spring material.

24. The duodenal/small intestinal insert of claim 21, wherein the umbrella cage is constructed from a spring material.

25. The duodenal/small intestinal insert of claim 1 wherein the elongated solid central shaft member can be straightened for introduction into the duodenum and then returned to the pre-set shape.

26. The duodenal/small intestinal insert of claim 1 wherein the pre-set shape assists in restricting distal migration of the duodenal/small intestinal insert.

27. The duodenal/small intestinal insert for treating obesity according to claim 1 wherein the at least one flow reduction element is formed from a sleeve coupled to the elongated solid central shaft member.

28. The duodenal/small intestinal insert for treating obesity according to claim 27 wherein at least a portion of the sleeve slides in relation to the elongated solid central shaft member.

29. The duodenal/small intestinal insert for treating obesity according to claim 27 the at least one flow reduction element protrudes from the elongated solid central shaft member.

30. The duodenal/small intestinal insert of claim 1 wherein the pre-set shape such that the curved longitudinal axis mimics the curvature between two portions of the duodenum.

31. The duodenal/small intestinal insert of claim 30 wherein the two portions of the duodenum are a duodenal bulb and the vertical duodenum.

32. The duodenal/small intestinal insert for treating obesity according to claim 30 wherein the two portions of the duodenum are a vertical duodenum and a horizontal duodenum.

33. A method of using a duodenal insert to reduce the flow of a food through a small intestine of a patient, the duodenal insert including an elongated solid central shaft member having a proximal end and a distal end and a curved longitudinal axis extending from the proximal end to the distal end, the duodenal insert further including an anchoring member engaged with the proximal end of the elongated solid central shaft member, wherein the elongated solid central shaft member has a pre-set shape such that a portion of the curved longitudinal axis mimics an angulation of the duodenum, the method comprising the steps of:
straightening the elongated solid central shaft member from the pre-set shape;
after the straightening, advancing the duodenal insert along an alimentary canal until the distal end of the elongated solid central shaft member is in the duodenum of the patient;
returning the elongated solid central shaft member to the pre-set shape after the advancing; and
expanding a flow reduction element carried by the elongated solid central shaft member of the duodenal insert when the flow reduction element is distal to a pylorus, wherein after the flow reduction element is expanded within the duodenum the food passing through the duodenum passes between a duodenal wall and the outside of the flow reduction element.

34. A method of using a duodenal insert to reduce the flow of a food through a small intestine of a patient according to claim 33 wherein the advancing step is performed using a working channel of an endoscope.

35. A method of using a duodenal insert to reduce the flow of a food through a small intestine of a patient according to claim 33 wherein the expanding step is performed when the flow reduction element is advanced out of a working channel of an endoscope.

36. A method of using a duodenal insert to reduce the flow of a food through a small intestine of a patient according to claim 33 further comprising: deploying the anchoring member into a portion of a stomach proximal to a pylorus of the patient.

37. A method of using a duodenal insert to reduce the flow of a food through a small intestine of a patient according to claim 36 wherein the deploying the anchoring member step positions the anchoring member within an antrum of a stomach.

38. A method of using a duodenal insert to reduce the flow of a food through a small intestine of a patient according to claim 36 wherein when the anchoring member is in the stomach, the elongated solid central shaft member passes through a pyloric valve while allowing the pyloric valve to function.

39. A method of using a duodenal insert to reduce the flow of a food through a small intestine of a patient according to claim 33 wherein the advancing step places the distal end of the elongated solid central shaft member into a horizontal duodenum of the patient.

40. A method of using a duodenal insert to reduce the flow of a food through a small intestine of a patient according to claim 33 wherein after the expanding step the flow reduction element has a diameter sized to partially block a flow of food through the duodenum of the patient.

41. A method of using a duodenal insert to reduce the flow of a food through a small intestine of a patient according to claim 33 wherein the straightening is performed such that the duodenal insert can be inserted with an endoscope.

42. A duodenal/small intestinal insert for treating obesity in humans by reducing the desire for eating, comprising:
an elongated solid central shaft member, said elongated solid central shaft member having a proximal end and a distal end and a curved longitudinal axis extending from the proximal end to the distal end, wherein the elongated solid central shaft member has a pre-set shape prior to insertion in the gastrointestinal tract such that a portion of the curved longitudinal axis mimics an angulation of the duodenum and returns to said pre-set shape after insertion into the gastrointestinal tract, and wherein the elongated solid central shaft does not have a lumen extending from the proximal end to the distal end such that, in use in the gastrointestinal tract, chyme flows on the outside of the elongated solid central shaft member;
an anchoring member engaged with the proximal end of said elongated solid central shaft member; and
at least one flow reduction element coupled to the elongated solid central shaft member at a distance from the anchoring member such that when the anchoring member is in an antrum of the stomach the at least one flow reduction element is positioned within a small intestine.

43. The duodenal/small intestinal insert of claim 42, wherein the elongated solid central shaft member is formed from a shape memory material.

44. The duodenal/small intestinal insert of claim 42, wherein the flow reduction element is concentric with the elongated solid central shaft member.

45. The duodenal/small intestinal insert of claim 42, wherein the flow reduction element is eccentric to the elongated solid central shaft member.

46. The duodenal/small intestinal insert of claim 42, wherein the flow reduction element occupies about 30-80% of the small intestine diameter.

47. The duodenal/small intestinal insert of claim 42, wherein the flow reduction element occupies about 40-60% of the small intestine diameter.

48. The duodenal/small intestinal insert of claim 42, wherein the flow reduction element is sized to restrict but not occlude the movement of digested food through the small intestine.

49. The duodenal/small intestinal insert of claim 42, wherein the flow reduction element self expands from a first volume to a second volume when unrestrained.

50. The duodenal/small intestinal insert of claim 49, wherein the flow reduction element is formed from open or closed cell foam.

51. The duodenal/small intestinal insert of claim 49, wherein the flow reduction element is impregnated with pharmacologics, biochemicals, alimentary lipids, alimentary peptides or metabolic substances.

52. The duodenal/small intestinal insert of claim 51, wherein the pharmacologics, biochemicals, alimentary lipids, alimentary peptides or metabolic substances are released into the small intestine over time.

53. The duodenal/small intestinal insert of claim 42, wherein the anchoring member is a toroid shaped anchoring member configured to reside in the antrum of the stomach and when fully deployed restricts distal migration of the elongated member.

54. The duodenal/small intestinal insert of claim 42, wherein the anchoring member comprises two or more balloons eccentrically arranged on the proximal end of the elongated solid central shaft member.

55. The duodenal/small intestinal insert of claim 54, wherein the balloons are inflatable and their combined diameter is larger than the opening of the pylorus.

56. The duodenal/small intestinal insert of claim 42, wherein the anchoring member comprises two or more volume occupying members that self expand from a first volume to a second volume when unrestrained and their combined diameter is larger than the opening to into the pylorus.

57. The duodenal/small intestinal insert of claim 42, wherein the anchoring member comprises:
   a collapsible, umbrella cage with a closed end and an open end, said closed end connected to the proximal end of the elongated solid central shaft member.

58. The duodenal/small intestinal insert of claim 57, wherein the umbrella cage is constructed from a shape memory material.

* * * * *